(12) United States Patent
Dwyer-Joyce et al.

(10) Patent No.: US 7,066,027 B2
(45) Date of Patent: Jun. 27, 2006

(54) METHOD AND APPARATUS FOR DETERMINING THICKNESS OF A LUBRICANT FILM

(75) Inventors: Robert Sean Dwyer-Joyce, Hope Valley (GB); Cornelius Joseph Donohoe, Cumbria (GB); Bruce Walton Drinkwater, Bristol (GB)

(73) Assignees: University of Sheffield, Sheffield (GB); University of Bristol, Bristol (GB)

( * ) Notice: Subject to any disclaimer, the term of this patent is extended or adjusted under 35 U.S.C. 154(b) by 0 days.

(21) Appl. No.: 10/362,813

(22) PCT Filed: Aug. 24, 2001

(86) PCT No.: PCT/GB01/03800

§ 371 (c)(1),
(2), (4) Date: Aug. 25, 2003

(87) PCT Pub. No.: WO02/18872

PCT Pub. Date: Mar. 7, 2002

(65) Prior Publication Data

US 2004/0045356 A1 Mar. 11, 2004

(30) Foreign Application Priority Data

Aug. 29, 2000 (GB) .................................. 0021114.4

(51) Int. Cl.
*G01N 29/10* (2006.01)

(52) U.S. Cl. ............................. 73/579; 73/597; 73/602; 73/644

(58) Field of Classification Search .................. 73/579, 73/597, 602, 593, 659, 660, 615, 644, 665, 73/627, 629

See application file for complete search history.

(56) References Cited

U.S. PATENT DOCUMENTS

| | | | | |
|---|---|---|---|---|
| 3,435,381 A | * | 3/1969 | Tournois | 333/145 |
| 3,952,566 A | | 4/1976 | Jacobson | |
| 4,338,821 A | * | 7/1982 | Dion | 73/603 |
| 5,176,034 A | | 1/1993 | Hazony et al. | |
| 5,237,516 A | * | 8/1993 | Heyman | 702/42 |
| 5,942,690 A | * | 8/1999 | Shvetsky | 73/660 |
| 5,959,189 A | * | 9/1999 | Jeng et al. | 73/10 |
| 6,122,966 A | * | 9/2000 | Goodman et al. | 73/593 |
| 6,339,961 B1 | * | 1/2002 | Goodman et al. | 73/593 |
| 6,360,610 B1 | | 3/2002 | Jarzynski et al. | 73/627 |
| 6,561,316 B1 | * | 5/2003 | Graf et al. | 184/38.4 |

FOREIGN PATENT DOCUMENTS

WO     WO 02/18872 A1     7/2002

OTHER PUBLICATIONS

*International Search Report* for corresponding PCT application No. PCT/GB 01/03800 filed on Aug. 24, 2001. Report dated Dec. 11, 2001.

(Continued)

*Primary Examiner*—Hezron Williams
*Assistant Examiner*—Jacques M Saint-Surin
(74) *Attorney, Agent, or Firm*—Marshall, Gerstein & Borun LLP

(57) ABSTRACT

A method and apparatus of determining the thickness of a lubricant film disposed between two bodies by measuring and performing a frequency spectrum analysis on a reflected or transmitted part of an ultrasound wave propagated towards said film is disclosed.

16 Claims, 18 Drawing Sheets

OTHER PUBLICATIONS

Kinra V K et al., "Simultaneous Measurement of the Acoustical Properties of Thin-Layered Medium: The Inverse Problem" Journal of the Acoustical Society of America, American Institute of Physics, New York, US, vol. 95, No. 6, Jun. 1, 1994, pp. 3059-3074.

Drinkwater B et al., "Measurement of the frequency dependence of the ultrasonic reflection coefficient from thin interface layers and partially contacting interfaces" Ultrasonics, IPC Science and Technology Press LTDL Guildford, GB, vol. 35, No. 7, Nov. 1, 1997, pp. 479-488.

Pialucha T et al., "The Detection of Thin Embedded Layers Using Normal Incidence Ultrasound" Ultrasonics, IPC Science and Technology Press Ltd. Guildord, GB, vol. 32, No. 6, 1994, pp. 431-440.

\* cited by examiner

METHOD AND APPARATUS FOR DETERMINING THICKNESS OF A LUBRICANT FILM

FIELD OF THE DISCLOSURE

This disclosure relates to methods of determining the thickness of a lubricant film and apparatus therefor.

BACKGROUND TO THE DISCLOSURE

Knowledge of the lubricant film thickness between moving machine elements (bearings) is essential for bearing design in order to avoid premature failure, to achieve greater efficiency and to prolong the life of machines. Online measurement of lubricant films in bearings is desirable since this gives immediate feedback on machine performance. Lubricant films found in, engineering components have thicknesses ranging from hundreds of microns down to several nanometers. Measurements on these scales (especially at the thin end) are very difficult and have been a major research issue for many years.

There are a number of known techniques for lubricant film measurement and these have recently been reviewed [in Spikes H A. Thin films in elastohydrodynamic lubrication: the contribution of experiment. *Proceedings of the Institution of Mechanical Engineers*, 213 J:PP. 335–352, (1999)]. They can be divided broadly into electrical and electromagnetic methods.

Electrical Techniques

Contact Resistance consists of measuring the electrical resistance of asperities within a contact patch. Essentially, this technique only provides a measure of lubricant film failure as it is only when the film fails that asperities will come into contact.

The Capacitance method involves measuring the capacitance between two lubricant-separated surfaces. Provided that the dielectric constant of the film is known, the film thickness can be determined. This commonly used method only provides average values of the film thickness. It is sometimes possible to mathematically predict more local values for certain bearing geometries. Alternatively, parts of the bearing can be electrically isolated from each other, making localised measurements possible but it then becomes difficult to align the isolated parts properly. The thickness may be similarly determined from Variable Reluctance measurements but again, it is difficult to determine film thicknesses locally.

Microtransducers are used in thin film measurements found in rolling element bearings such as ball-bearings. A typical microtransducer arrangement consists of a bearing surface coated with an insulating material. A thin strip of metal is then deposited by sputtering onto the insulated surface. An electrical current is then passed through this metal and it acts as a strain gauge when the surface deforms. This enables measurement of contact pressure which in some cases can be used to deduce information about the presence of a lubricant film. The two bearing surfaces need to be electrically isolated which severely restricts the scope for taking measurements on real engineering components.

Displacement Measurement Techniques

Other electrical techniques involve the use of displacement transducers to macroscopically monitor the movement of the bearing parts with respect to one another. Examples of such methods are the positioning of Linear Variable Displacement Transducers (L VDTs) against different external parts of the bearing and capacitance measurements on out-of-contact parts of the bearing. Again, these techniques provide limited localised information and are only suitable for measuring thick films (>20 µm). Since the transducers are placed outside of the bearing contact, they are prone to inaccuracies caused by differential thermal expansion of components (in the presence of thermal gradients) and vibrations. A further problem is that the LVDTs have to be placed against moving parts of the bearing.

Electromagnetic Radiation Techniques

Optical Interferometry involves passing a beam of monochromatic light through a flat piece of glass with a semi-reflective coating, through the film and onto the second bearing surface. Some of the beam reflects off the coated glass without passing through. Interference occurs between the beam that reflects off the second bearing surface and the one which is reflected straight off the coated glass. The film thickness can be determined from the wavelength of light used and the fringe order.

Since the path difference for the interference to occur needs to be at least half the wavelength of the light used, the limit of resolution of this technique is a quarter of the wavelength. To overcome this limitation, Ultrathin Film Interferometry was developed. This uses a "spacer layer" of silica placed beneath the chromium layer to permit optical interference to occur even when there is no oil present.

The Optical Densitrometry technique makes use of the fact that most lubricants exhibit some degree of opacity. The amount of light attenuated increases with the film thickness thereby offering a means of measuring film thickness.

Laser Fluorescence involves mixing the oil with a substance which fluoresces under a laser beam. The intensity of the resulting light emitted thus increases with film thickness, allowing a measurement of the thickness to be made.

In summary, the electromagnetic radiation based techniques allow more localised measurements to be made but suffer from the disadvantage that some type of window arrangement is necessary in order to admit the radiation. These methods are used successfully in laboratory research settings to study lubricant behaviour.

The above techniques have associated disadvantages. Optical techniques require one of the moving parts to be wholly or partly constructed from a transparent material such as glass. If a glass window is used in a metal bearing, it will inevitably have different thermal expansion properties to that of the metal, leading to difficulties in keeping the two surfaces aligned. In situations where the film thickness is of the order of tens of microns, there is little scope for tolerance of such misalignment. The electrical capacitance method is well known and widely used but only provides an average value of film thickness between two surfaces. It is possible to insert capacitive probes that are insulated from the surrounding material to enable local measurements to be taken. Again, this leads to alignment problems as are found with glass windows used for optical measurements.

In accordance with one aspect of the disclosure a method and apparatus for determining the thickness of a lubricant layer or film that alleviates the above-described problems are disclosed. The disclosure described herein enables measurement, using novel test apparatus and a range of data processing techniques, of lubricant film thickness over all expected scales i.e. from hundreds of microns down to several nanometers.

The ability to measure over a wide range of expected film thickness levels encountered in machine components (such as those operating in the boundary, elastohydrodynamic, hydrodynamic, and hydrostatic lubrication regimes) means that the teachings of the disclosure can be used, for example, in many lubricated machine components, such as journal bearings, roller element bearings, piston-ring liners, cam-tappets, wet seals, thrust pad bearings and gear teeth.

Summary of the Disclosure

According to a first aspect of the present invention disclosure, there is provided a method of determining the thickness of a lubricant film disposed between two bodies by measuring and performing a frequency spectrum analysis on a reflected or transmitted part of an ultrasound wave propagated towards said film.

By using ultrasound to determine the thickness of a lubricant layer or film, the advantage is given of not requiring optically transparent surfaces and being non-invasive. The film measured is thus that which is actually present between the two bodies and is no way modified by the presence of a transducer. The technique thus has the potential for use in a wide range of lubricated machine parts; both as a research tool to assist in component development and as an on-line monitoring tool for running components.

Preferably, the ultrasound wave is propagated through the first of said two bodies substantially normal to an interface between said lubricant film and said first body ("the first interface"). Ideally, the method further comprises the step of detecting the proportion of the ultrasound wave that is reflected at said interface.

Preferably, the method further comprises the step of detecting the proportion of the ultrasound wave which is reflected at the interface between the second of said two bodies and the lubricant film ("the second interface").

Alternatively, the method further comprises the step of detecting the proportion of the ultrasound wave which is transmitted through said two bodies and lubricant film.

Preferably, a single transducer is used both to generate the ultrasound wave and detect the reflection and/or attenuation thereof.

Preferably, the ultrasound wave is propagated through a coupling medium towards said first body. In a further preferred form, said coupling medium comprises water.

For intermediate thickness lubricant films (10–60 microns approx.), preferably, the thickness is determined by performing a Fourier transform on the time domain signal of the ultrasound wave reflected from the lubricant film. This frequency spectrum is analysed to determine its shape and the presence of any resonant frequencies. The resonant frequency can be used directly to obtain the layer thickness. Alternatively, the frequency spectrum shape is compared to a continuum model of the lubricant layer and its response to an ultrasonic wave.

For thin lubricant films (<10 microns approx.) preferably, the thickness is determined by quantifying the stiffness of the liquid layer from the reflection of the ultrasonic wave in conjunction with a spring model and/or continuum model of the two bodies and interface assembly.

Alternatively, the thickness of thin lubricant film is determined by quantifying the attenuation of a shear ultrasonic wave in the lubricant film.

Preferably, said two bodies are parts of a lubricated bearing such as a journal bearing, roller element bearing, piston-ring liner, cam-tappet, wet seal, thrust pad bearing or gear teeth.

According to a second aspect of the disclosure, there is provided apparatus for performing the method described above comprising means for generating an ultrasound wave and propagating same towards a lubricant film whose thickness it is desired to determine; a detector for detecting a reflected or transmitted part of said ultrasound wave; and a processor for determining the thickness of the lubricant film by performing a frequency spectrum analysis on the reflected or transmitted part of said ultrasound wave.

BRIEF DESCRIPTION OF THE DRAWINGS

Preferred embodiments of the present disclosure will now be more particularly described, by way of example only, with reference to the accompanying drawings in which.

DESCRIPTION OF THE PREFERRED EMBODIMENTS

This disclosure uses ultrasound waves to measure the film thickness of a lubricated contact. The ultrasound wave is generated by a transducer in which a piezo-electric element is excited by an electrical pulse of finite duration. The pulse is then switched off and the same transducer measures returning echoes.

The transducer which creates the pulse does not necessarily always have to measure the returning echoes. Other transducers can be mounted at different locations to receive transmitted and/or reflected signals.

Figure 1:
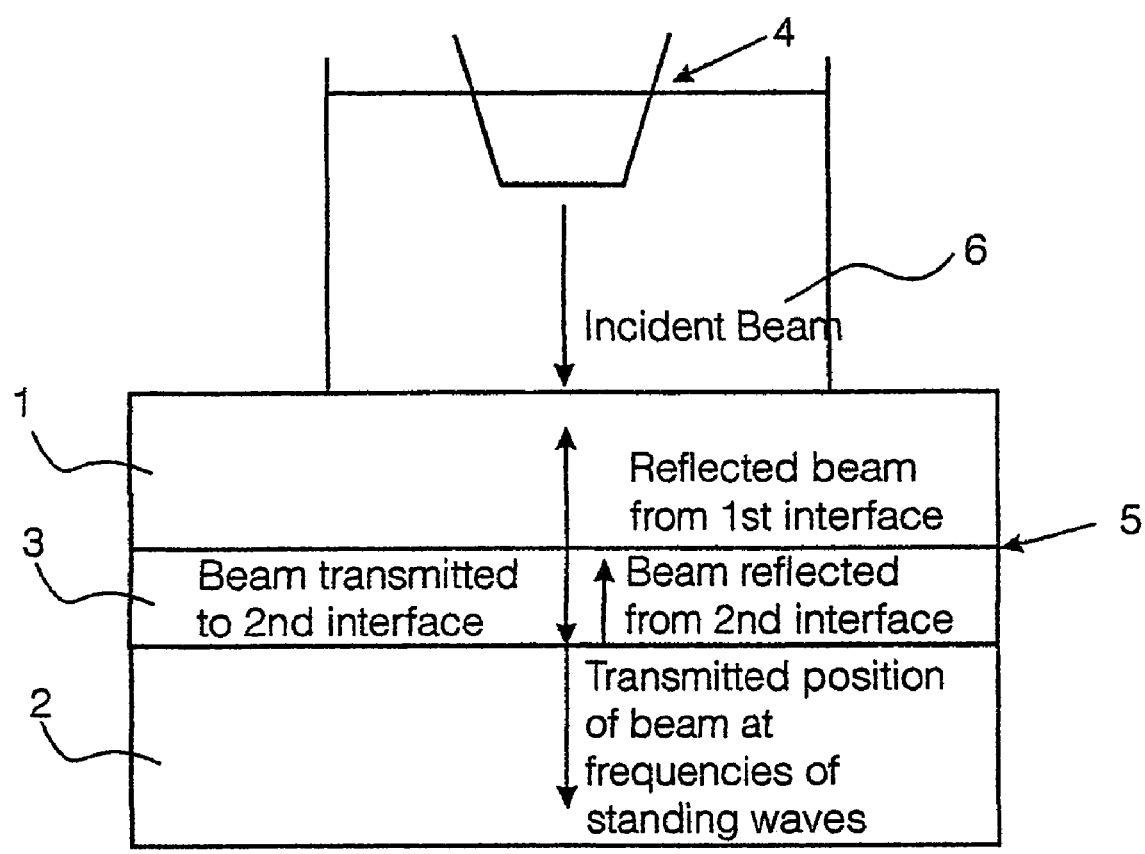
FIG. 1 is a schematic view of a transducer positioned to measure the thickness of a lubricant film between two solid bodies.

Taking the case of two solid bodies 1, 2 separated by a lubricant layer or film 3 as shown in FIG. 1, an incident beam is propagated through a coupling medium 6 (in this case water) by a transducer 4. The ultrasound wave (or signal) is propagated through the first body 1, towards the film 3 and normal to the interface 5 between the film 3 and the first body 1. A proportion of the wave amplitude is reflected back towards the transducer 4 and the remainder is transmitted through the layer to the second body 2. Of the signal that reaches the second body 2, a proportion of the wave is again reflected and a proportion transmitted.

The echoes coming from the interface 5 between the first solid body 1 and the film 3 are those which are most relevant in determining the film thickness. The main echo of interest is often immediately followed by a series of smaller echoes representing successive reverberations within the film. The main echo of interest and the succession of reverberations which follows can be magnified and zoomed in upon in detail using a modern digital oscilloscope and the data downloaded to a computer for processing.

There are three models with which the response of an interfacial layer to an ultrasonic pulse can be predicted:

Model (a): The time of flight model. The time between the pulse being reflected from the lubricant layer front face (the first interface) and lubricant layer back face (the second interface) can be used to determine the thickness of the layer if the speed of propagation is known. In practice, this model is only suitable for application with thick lubricant layers where the measuring frequencies are high enough such that individual pulses can be resolved.

Model (b): The spring model. The lubricant layer can be modelled as a spring interposed between two solid bodies [Drinkwater, B. W., Dwyer-Joyce, R. S., and Cawley, P., (1996), "*A Study of the Interaction between Ultrasound and a Partially Contacting Solid—Solid Interface*", Proc. Roy. Soc. A, Vol. 452, No. 1955, pp. 2613–2628, London]. The displacements on either side of the interface are written in terms of the local pressures (the pressure is proportional to the differential of the displacement). These displacements are caused by the incident, reflected, and transmitted wave plus the extra displacement of the interface layer. The interface displacement is given by the transmitted wave pressure divided by the interface layer stiffness. The reflection coefficient spectrum, R is obtained from the reflected wave pressure when the incident wave pressure is set to unity. This yields an expression relating R to the stiffness of the interface, K:

$$K = \pi f \rho c \sqrt{\frac{1}{R^2} - 1}$$

Measured reflection spectra can thus be converted to interface stiffness values; from which layer thickness (for thin layers) is readily obtained.

Model (c). The continuum model. The lubricant layer can be modelled as continuum and a full wave equation developed [Pialucha T and Cawley P. The detection of thin embedded layers using normal incidence ultrasound. *Ultrasonics*, 32(6):pp. 431–440, (1994)]. The wave displacements and pressures in each of the media (first solid body, layer, and second solid body) are mathematically expressed as summations of the incident displacements/pressures and those of any reflected pulses. The stresses and displacements immediately to either side of each of the boundaries (solid 1-layer and layer-solid 2) are then equated. This gives equations for the stress and displacement at any location within the three bodies. The reflection coefficient spectrum, R is obtained by setting the incident wave amplitude to unity. For a given film thickness and acoustic properties of the bodies, a reflection coefficient spectrum can be deduced. The layer thickness in the model can be changed to provide a series reflection spectra; matching one of these to a measured spectrum provides a method for layer thickness determination.

There are five principal experimental methods for measuring lubricant film thickness from the information thus captured.

Figure 2:
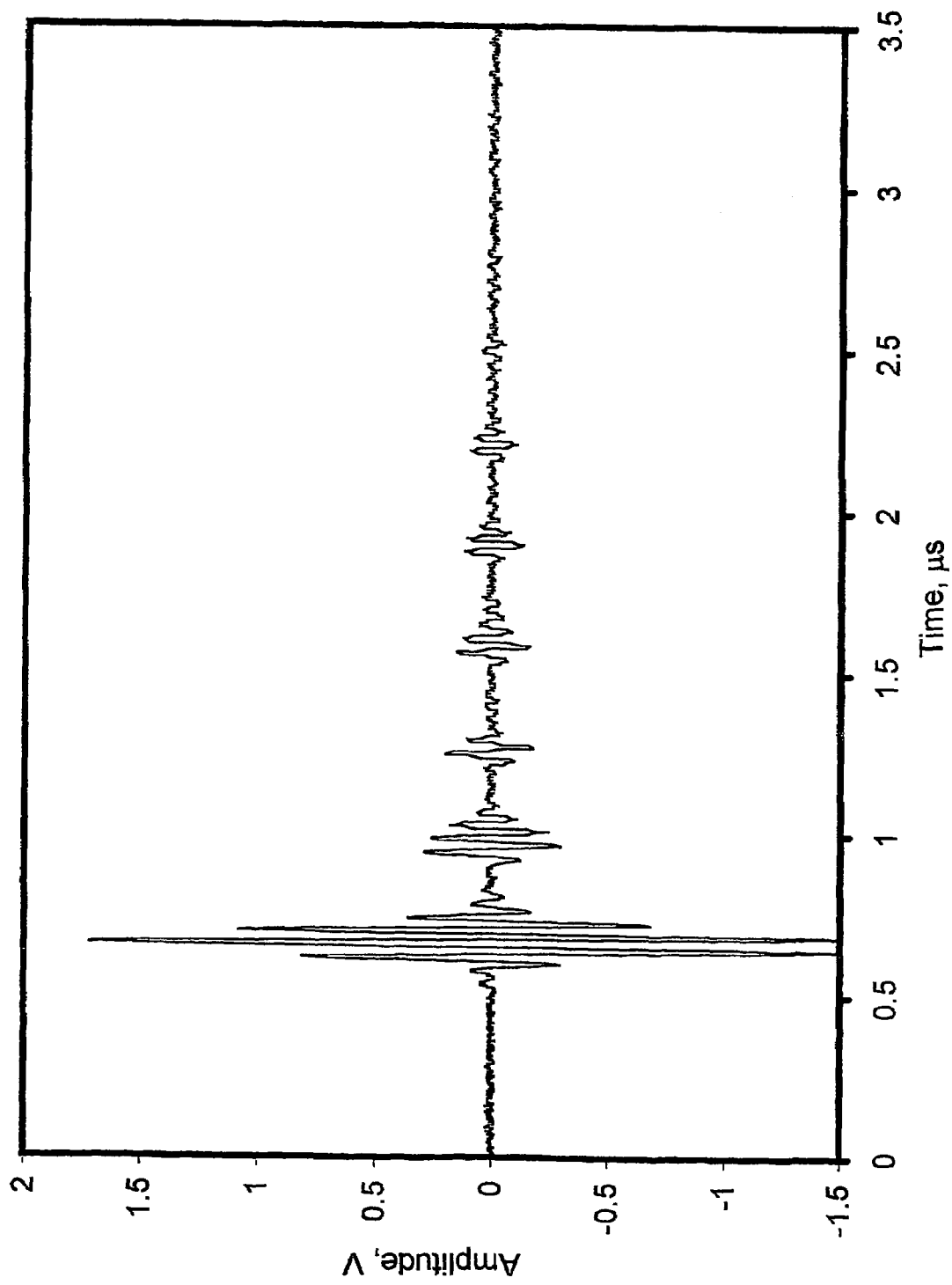
FIG. 2 is an example of the reverberations after the main echo of interest seen on an oscilloscope when the lubricant film is thick.

Method(i) The Time of Flight Method (thick lubricant films). If the lubricant film is sufficiently thick, a series of further echoes will immediately follow the main echo of interest from the first-body/film interface and will be seen on the oscilloscope. An example of such echoes is shown in FIG. 2. The echoes will then be sufficiently separated for the time interval between them to be resolved. The film thickness is then found by multiplying the speed of sound by the time interval between each repeated pulse. This is known as the Time of light method.

Method (ii) The Film Resonance Method (intermediate thickness film).

Figure 3:
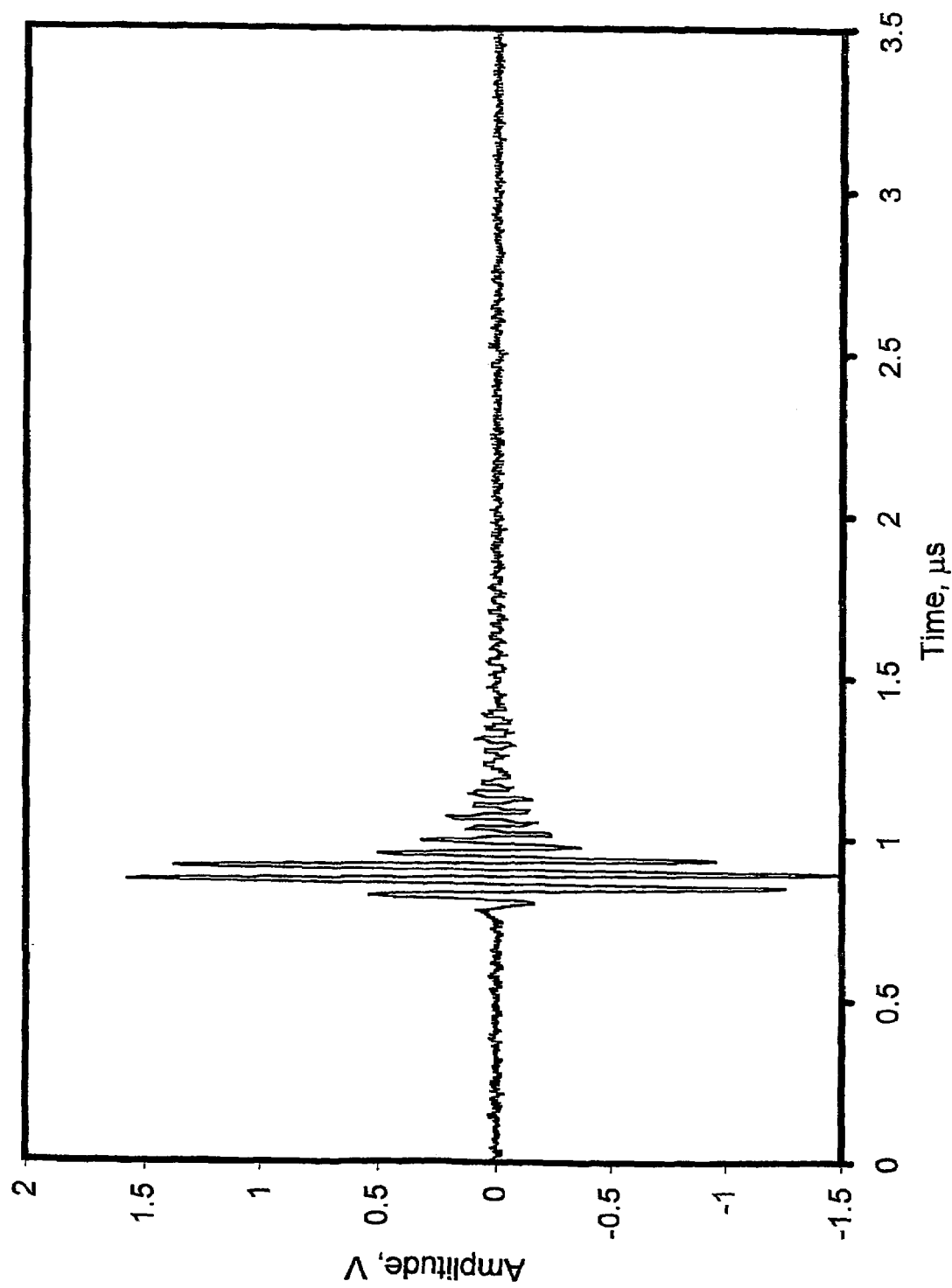
FIG. 3 is an example of the reverberations after the main echo of interest which are seen squeezed together when the film is thin.
Figure 4:
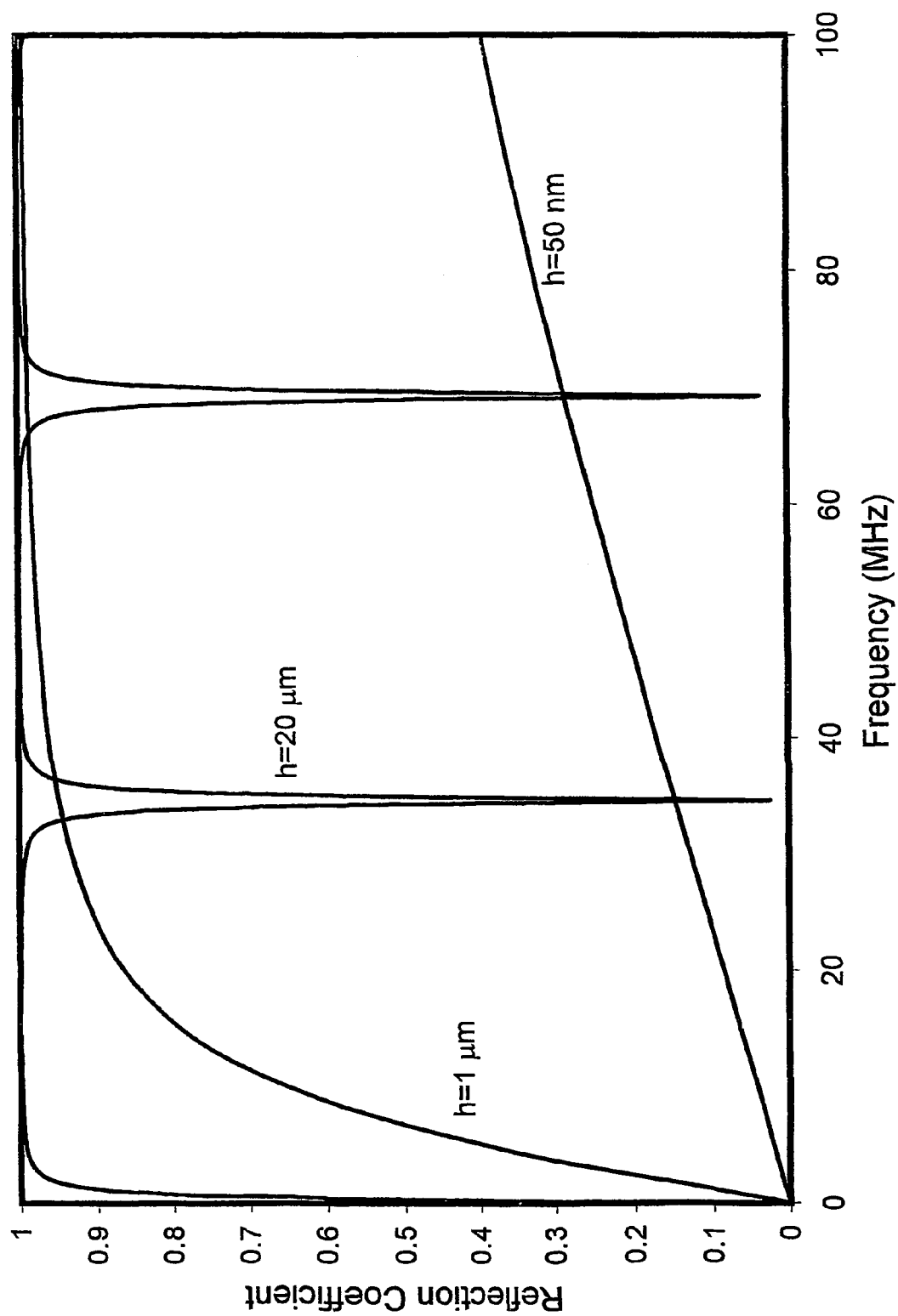
FIG. 4 shows reflection coefficient spectra predicted for a range of lubricant films. Depending on the thickness, either resonant troughs or a characteristic shape are observed.
Figure 5:
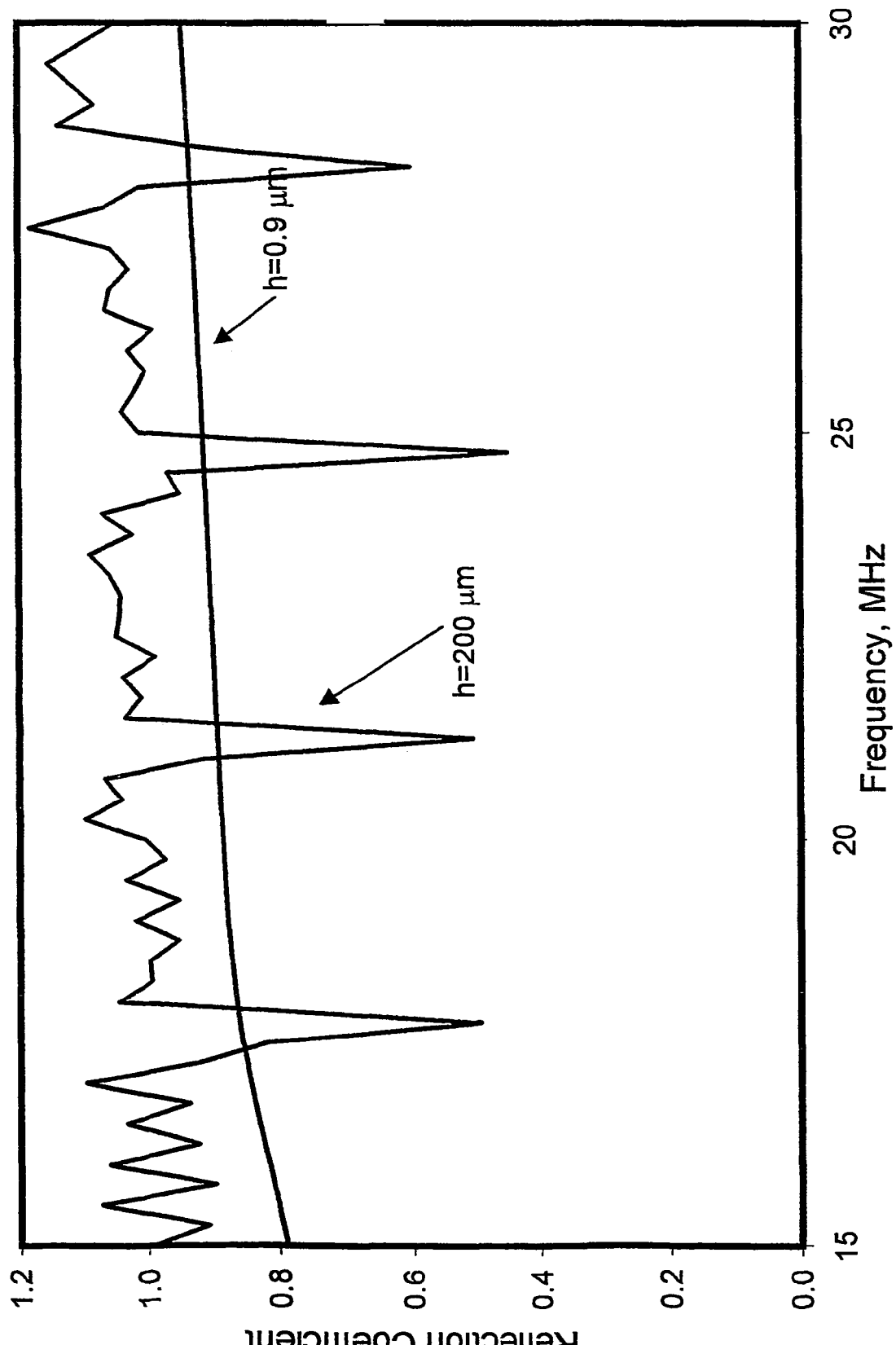
FIG. 5 shows typical measured reflection coefficient spectra predicted for a range of lubricant films.

In this case the successive echoes will appear to be squeezed together as in FIG. 3 such that individual echoes cannot be resolved. The captured echo is downloaded from the oscilloscope to a personal computer. The signal is converted from the time domain to the frequency domain by Fourier analysis. One or more sharp troughs in the amplitude at various frequencies are observed as shown in FIG. 4 (for a 25 micron film thickness). These resonant frequencies would appear as peaks in an equivalent transmission measurement. It is convenient to normalise this data by dividing by a reference reflection spectrum from an out of contact signal (i.e. no lubricant layer and no second body). FIG. 5 shows measured reflection coefficient spectra with clear resonant frequencies. Each of these frequencies corresponds to that of a standing wave (or resonance) within a layer. When standing waves occur, the pulse is transmitted to the second body at the frequency of the standing wave and the reflected wave amplitude is virtually zero (hence the trough). By taking the frequency difference between any two successive troughs, Δf, (or the frequency of occurrence of a single trough) the layer thickness is $$h = \frac{c}{2\Delta f}$$

(see [Krautkramer J. and Krautkramer H. *Ultrasonic Testing of Materials*, page 133. George Allen and Unwin Ltd, London, 1969], where c is the speed of sound in the liquid film. This method of measurement is hereinafter known as the Film Resonance Method.

Method (iii) The Liquid Spring Method (lubricant film tends to zero thickness).

In this case (as in case ii) the successive echoes cannot be resolved. Again the captured echo is downloaded and converted to the frequency domain by Fourier analysis. For thin lubricant films (those occurring in boundary and elastohydrodynamic regimes) the resonant frequency will be above that available from a standard ultrasonic transducer. Thus the reflected signal contains no resonant dips. In the limit (film thickness tending to zero), the lubricant layer can be considered as a spring and a spring model is used. The stiffness of the lubricant layer is obtained from the reflection coefficient spectrum. The stiffness of the layer, K, is related to the film thickness by a simple mechanics analysis of the elastic deformation of the layer, viz.:

$$K = \frac{\rho c^2}{h}$$

where p is the density and c is the acoustic velocity of the lubricant (at the pressure at which it is subjected to in the contact). The curve for a thickness of 50 nanometers on FIG. 4 shows the predicted relationship between reflection and frequency for this case. Similar curves on FIG. 5 are from measured data.

Method (iv) The Spectral Gradients Method (thin lubricant films). In this case the film is too thin for a resonance to occur but too thick for a spring model assumption to be used (i.e. outside of the linear region of dependence of reflection against frequency). For this case the full theoretical frequency spectrum of the wave interaction with the liquid/solid interfaces is produced using the continuum model. An example is shown as the curve for a 1 micron film thickness on FIG. 4. The film thickness is obtained by selecting a value such that the theoretical and experimental spectra map as closely as possible.

Method (v) If the film attenuates the ultrasound wave. Shear waves are strongly attenuated as they pass through a liquid layer. For thin films, measurement of the attenuation of the wave will give a method for determination of the thickness of liquid the wave has passed through. Additionally, lubricants near a surface and under the high pressures found in some types of bearing (operating in elastohydrodynamic regimes) are known to become more viscous and solid-like. They may therefore allow some shear wave transmission that can be used to predict lubricant film thickness.

The above five cases will span a wide range of film thickness dimensions. The method suitable for thin film measurements will cover boundary and elastohydrodynamic lubricated machine components. The intermediate and thick film methods will cover hydrodynamic and hydrostatic lubrication regimes.

The boundary between thick and thin film, and the choice of implementation of a particular method, depends on the acoustic properties of both the lubricant and the bodies through which the ultrasound is propagated. For typical industrial mineral oils lubricating steel surfaces the following approximate limits of operation apply;

| Time of Flight Method | >60 μm |
| Film Resonance Method | >10 μm |
| Spectral Gradients Method | 1–10 μm |
| Liquid Spring Method | 0.01–1 μm |

Experimental Apparatus

To demonstrate the utility of the disclosure, a series of test experiments have been performed. The test platforms consist of both tests on static lubricant films between laboratory specimens and dynamic tests on rotating machine bearings.

Figure 6:
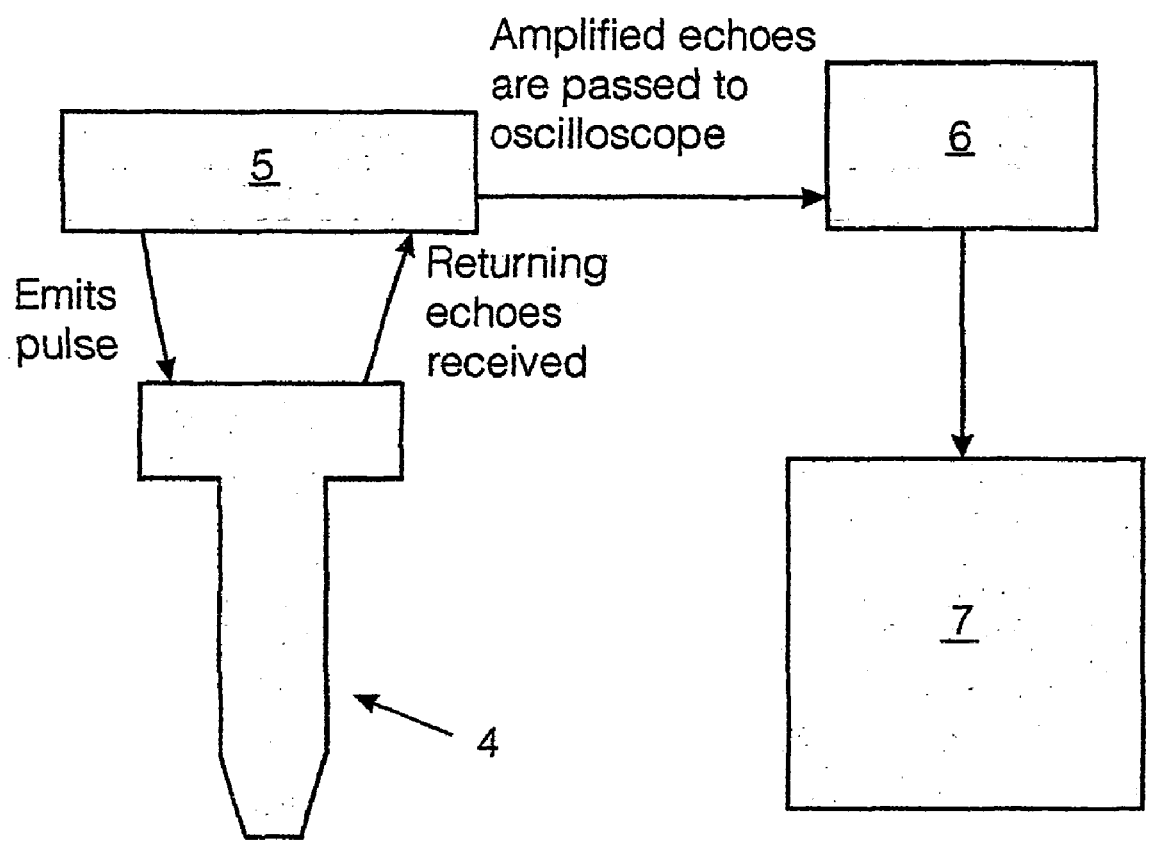
FIG. 6 is a schematic outline of the principal apparatus used.

The ultrasound control and data acquisition equipment is the same for all tests and comprises four main pieces of equipment, namely ultrasound transducers 4, an ultrasound pulser receiver (UPR) 5, a digital oscilloscope 6 and a computer 7 (see FIG. 6).

Ultrasound Transducers

The ultrasound transducers 4 (or probes) used, contain a piezo-electric element backed with a damping material (typically tungsten-loaded epoxy). The piezo-electric element, when excited by an electric potential, produces ultrasonic vibrations. In addition, when vibrated by some external source (e.g. a returning echo), it produces an electrical signal which is representative of the vibration.

Ultrasound transducers can be subdivided into two main categories, viz. longitudinal transducers and shear transducers. Longitudinal transducers emit longitudinal (tension-compression) waves that can propagate through liquids and solids. Shear transducers emit transverse or shear waves that are waves of shearing motion and propagate only through solids or for very short distances in extremely viscous liquids.

Both longitudinal and shear transducers are available in planar form (where the wave-emitting element surface is flat) or focussing form (where the element is concave) and which is capable of focussing the beam to a spot of typically 100 μm in size.

In the present disclosure, a broadband longitudinal focusing transducer was used with a centre-frequency of 25 MHz and a focal length of 53.8 mm. For the rotating ball tests a 50 MHz transducer was used to improve spacial resolution.

The Ultrasound Pulser Receiver (UPR)

A principal part of the ultrasound apparatus is the ultrasound pulser-receiver 5. This piece of electronic equipment provides an electrical pulse of finite duration (typically a few nanoseconds) which causes the transducer 4 to vibrate, producing a pulse of ultrasound waves. The electrical pulse is a signal of about 100 V. When the pulse is finished, the pulser-receiver 5 then quickly switches from pulse mode to receive mode. In this mode, the signal produced by returning ultrasound echoes that vibrate the piezoelectric element are received and amplified. The pulse repetition rate is the rate at which the pulser-receiver 5 switches from pulse to receive mode. It can be varied and could be for example set at 1 kHz.

The Digital Oscilloscope and Computer

A 50 MHz digital oscilloscope 6 was used to capture the received signal and download it to the computer 7. The digitisation level was 8-bit. Many returning echoes are apparent on the screen of the oscilloscope 6. Software was designed to extract an echo of interest, download it and process it to yield the film thickness. The echoes of interest in this case are usually those reflected from the interface 5 of the first body 1 and the lubrication film 3 (see FIG. 1). For film resonance, liquid spring, and spectral gradient measurements the software immediately carries out a Fast Fourier Transform (FFT) of the signal and performs a series of other processing tasks (based on the algorithms described above) which are necessary to provide an almost instant online film thickness measurement.

Experiments Used to Demonstrate Technique

Static Flat Plate Tests Static Flat Plate Tests

Figure 7:
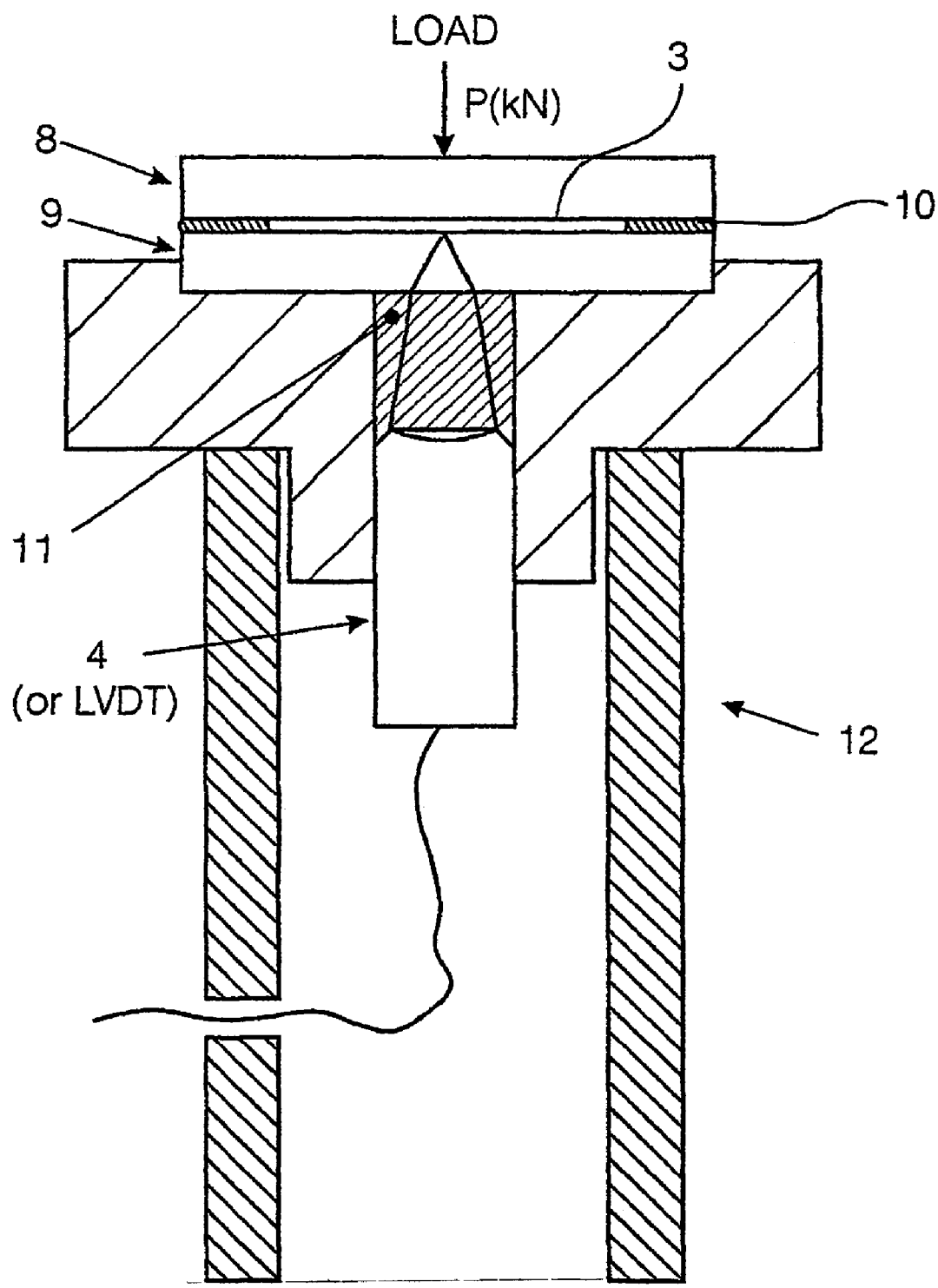
FIG. 7 is an outline of the principal components used in a flat plate testing rig.

The purpose of these tests is to verify that the technique works for thin layers of typical engineering lubricants sandwiched between solid pieces of material. The experimental apparatus used for these tests was designed to mimic the dimensions of films found in real moving bearings. These tests provided calibration data since it is easier to set up two stationary surfaces with a known gap between them than two dynamically moving surfaces. The apparatus used is shown schematically in FIG. 7.

Two types of static tests were conducted. The first test consisted of measuring the thickness of a lubricant film 3 between two flat plates 8, 9 separated by a shim 10 of 100 μm thickness. A coupling medium 11 (in this case water) was provided and the apparatus rested on a tubular stand 12. The probe 4 was placed under the bottom plate 9 and load was applied to the top plate 8 using a servo-hydraulic loading machine to deflect the plate 8 so as to vary the film thickness. The probe 4 was then removed and replaced by a linear variable displacement transducer (LVDT) in order to take separate measurements for comparison.

Figure 8:
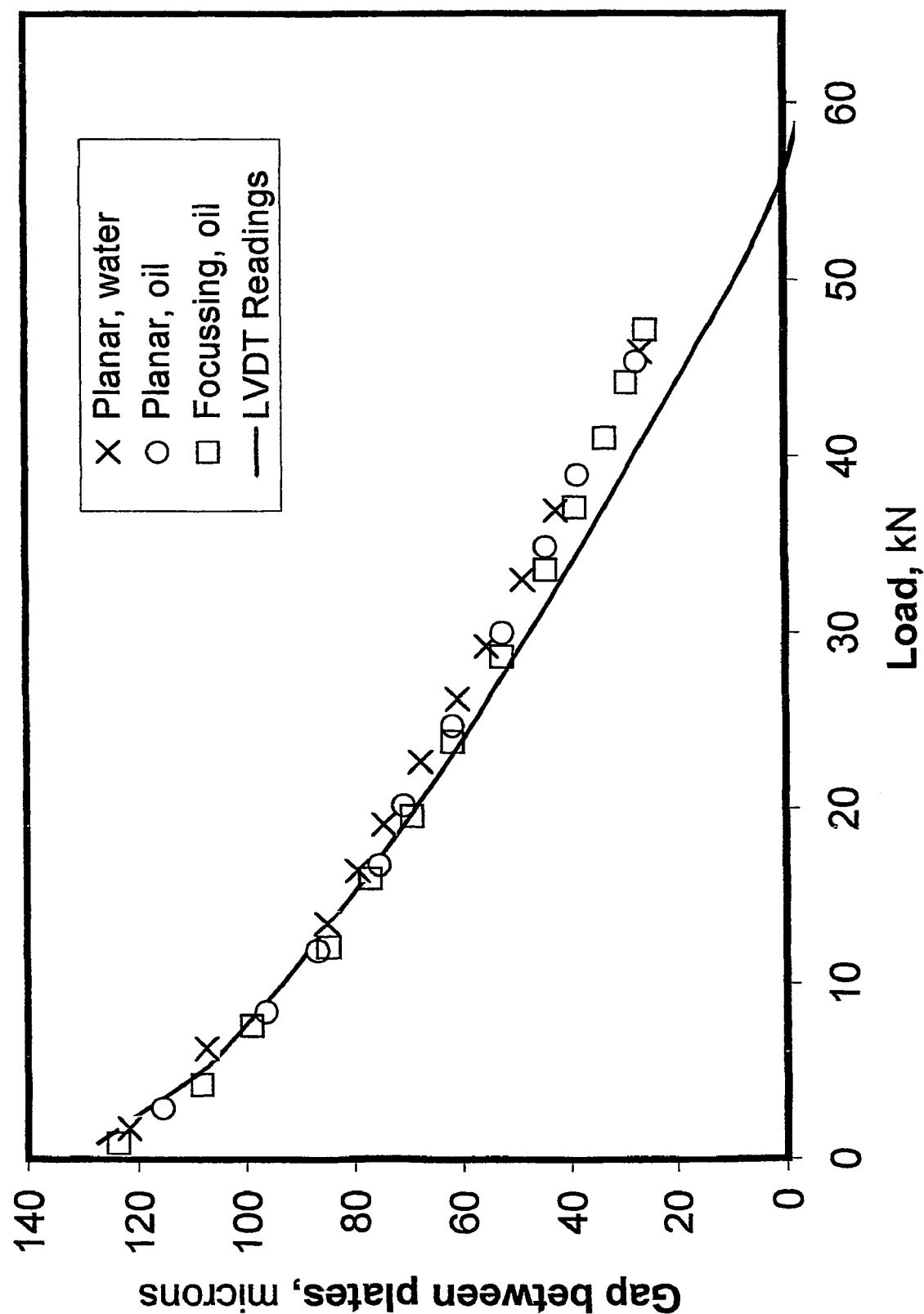
FIG. 8 shows the film thickness as a function of load for the flat plate deflection tests.

The results are shown in FIG. 8. In this work the film resonance method was employed. The minimum value of film thickness measured was 20 μm. This is the thinnest film that could be measured with the particular 25 MHz probe used. It is possible to measure thinner films by employing the Spectral gradient or liquid spring methods (or carrying out film resonance using higher frequency probes). Results are shown for films of water and oil using a planar longitudinal transducer and for oil using a focusing transducer. There is little difference in the results indicating that either type of transducer is suitable for such measurements. Results using an LVDT are also shown. The results of the ultrasound measurements deviate slightly from those using the LVDT. It is difficult to achieve static film at these low thicknesses. It is likely here that the LVDT back face measurement does not accurately reflect the gap between the two plates and hence the film thickness.

Static Curved-Geometry Tests

The purpose of these tests is to see whether curvature of the bearing surface (as encountered in plain journal bearings for instance) has any effect on the capacity of the ultrasound equipment to measure film thickness.

Figure 9:
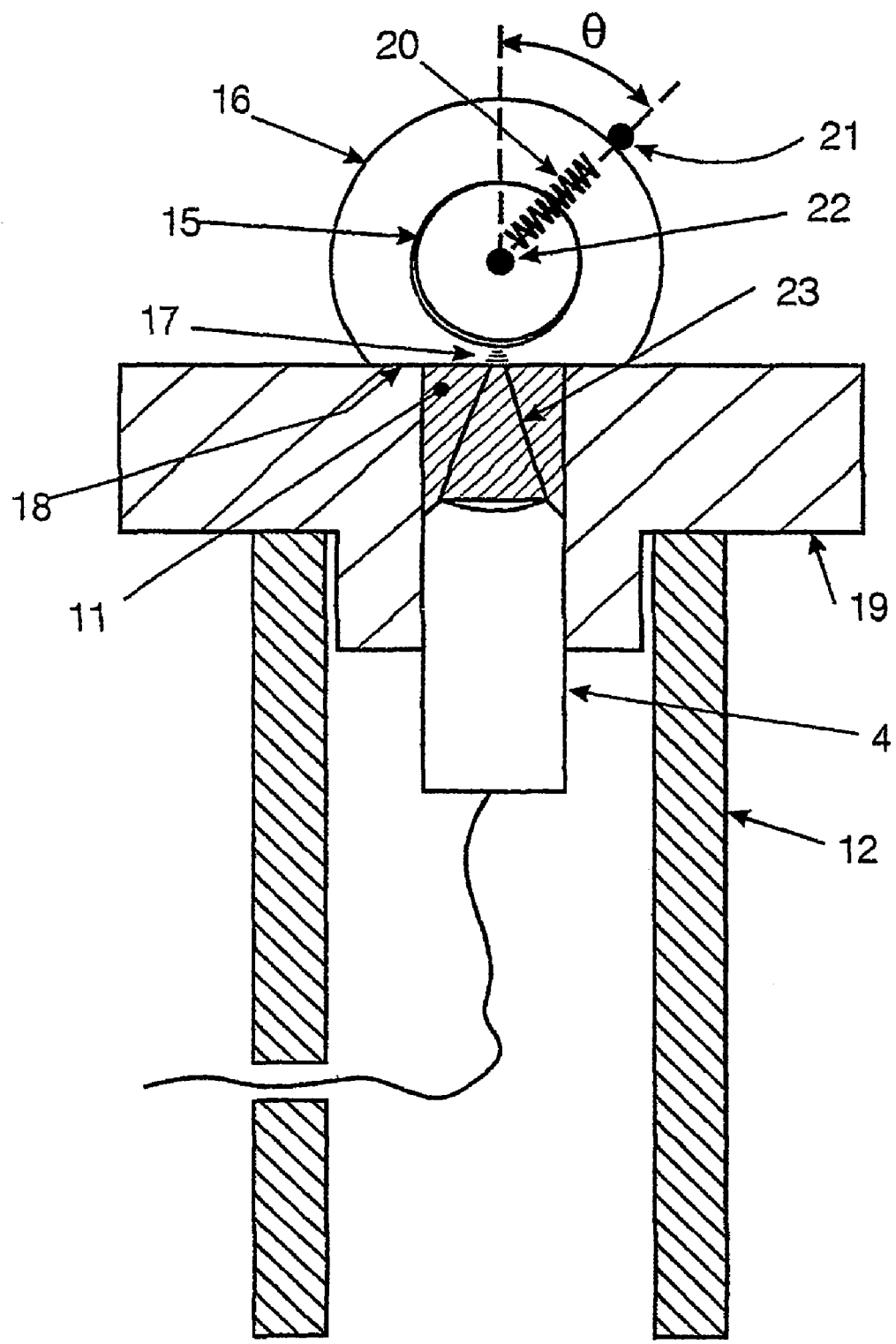
FIG. 9 is a schematic diagram of a static shaft test rig.

A rig was designed to mimic the geometry of a journal bearing. The rig, shown schematically in FIG. 8, consists of an aluminium shaft 15 eccentrically mounted within an aluminium collar 16. The collar 16 has a slightly larger diameter than the shaft so that a gap 17 is present between them. The collar 16, has a flat surface 18 machined on one side thereof which is mounted upon a flat testing platen 19 (shown in cross-section). The platen 19 holds the ultrasound transducer 4. Again, there is a coupling medium 11 and a tubular stand 12. The shaft 15 is biassed against the interior surface of the collar 16 by use of a pair of springs 20 (one at each end of the shaft). The springs 20 are biassed between a steel rod 21 placed against the outside of the collar 16 and a second steel rod 22 which passes through the centre of the shaft 15. By varying the angular position of the rod 21 on the outside of the collar 16, the angle 74 and hence the gap 17 between the bottom of the shaft 15 and the collar 16 can be varied. The normal shaft diameter chosen for this test is 20 mm. The ultrasound beam is represented by reference numeral 23 in FIG. 9.

Figure 10:
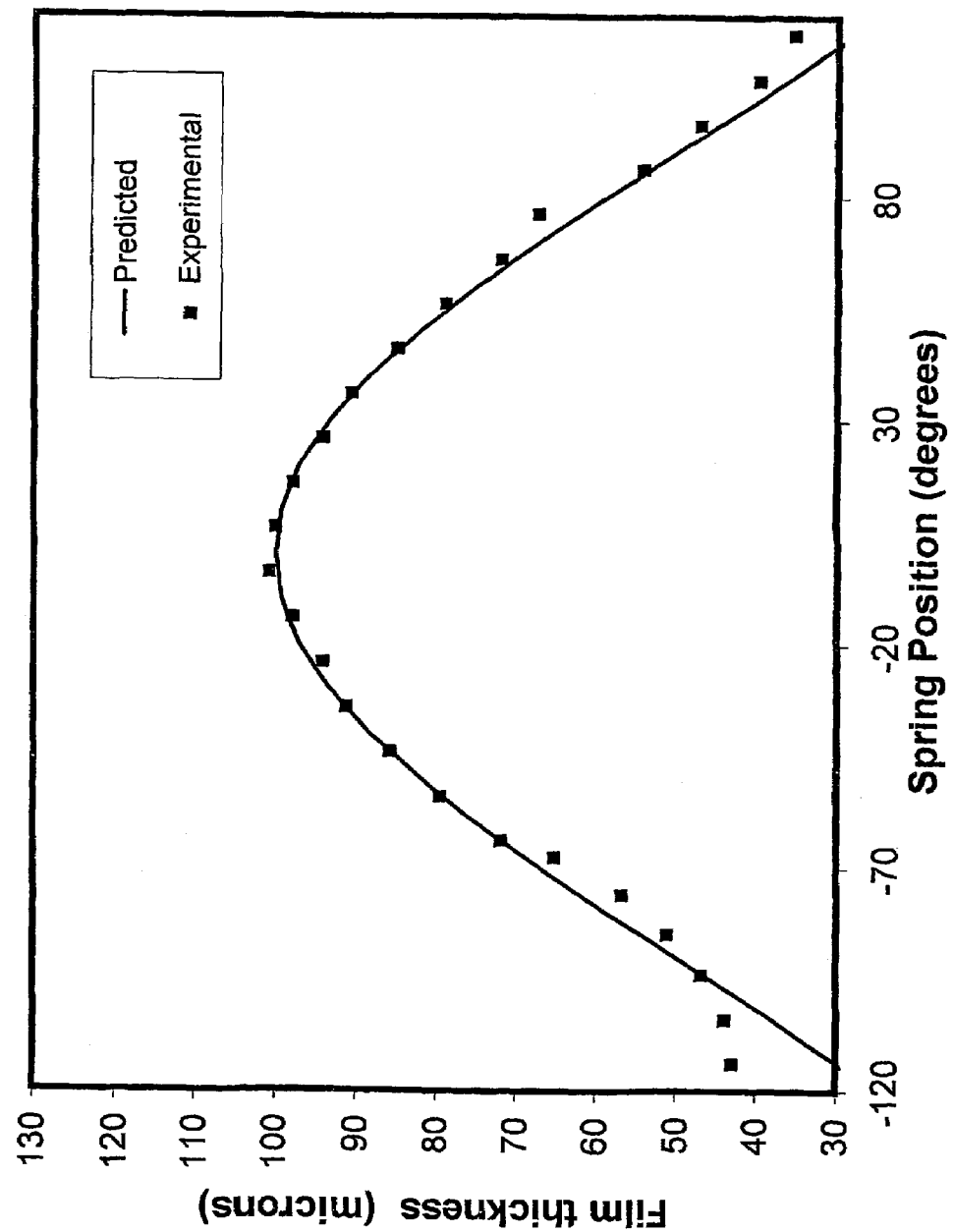
FIG. 10 shows the film thickness as a function of spring position for the static curved geometry tests.

The results of these tests are shown in FIG. 10. The gap between the eccentrically-mounted shaft and collar arrangement at the point of measurement, mathematically approximated by:

$$h = c(1 + \cos\theta)$$

is also shown. Again, good correlation is seen. Smaller film thicknesses are again hard to achieve due to surface tension of the fluid and machining accuracy of the shaft 15 and collar 16.

Journal Bearing Tests

The purpose of these tests is to construct an actual journal bearing rig which is capable of being run at different speeds and of carrying different bearing loads.

Figure 11A:
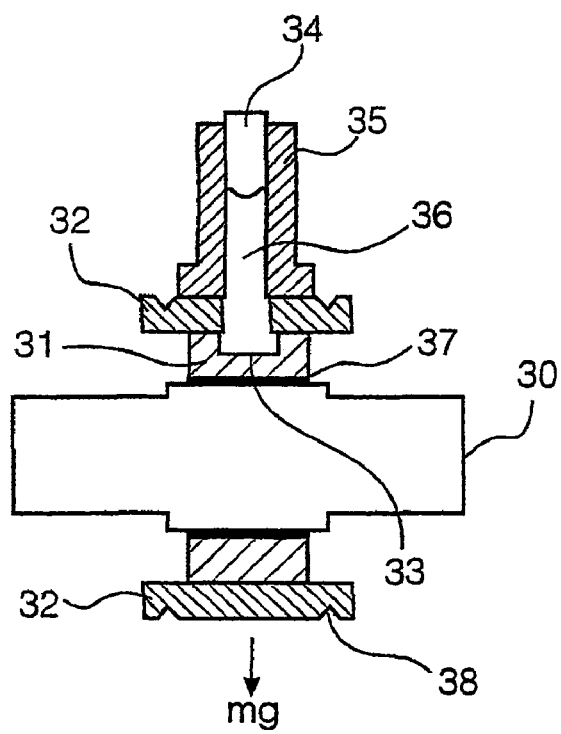
FIG. 11A is a schematic side cross-sectional view of a journal bearing rig.
Figure 11B:
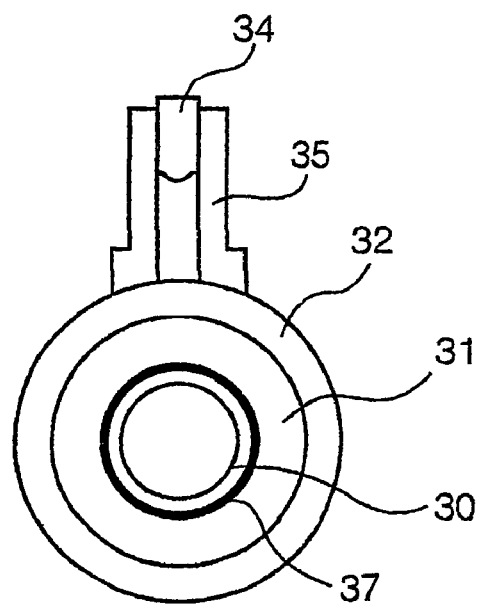
FIG. 11B is a schematic end view of the rig of FIG. 11A.

A simple hydrodynamic journal bearing test rig is shown schematically in FIGS. 11A and 11B. A cylindrical shaft 30 is machined from EN19 grade-steel. The diameter of the bearing section of the shaft is 28 mm. A "square" journal bearing arrangement is employed so that the bearing width is also 28 mm. The bearing bush 31 is made from a single piece of brass that is mounted by slight interference fit in a steel bush-holder 32. A small flat 33 is machined on part of the brass bush 31. In order to admit the ultrasound beam, an aperture 34 is drilled in the steel bush holder 32 to coincide with the position of the flat 33 on the brass bush 31. The ultrasound beam is focused on the bearing surface through this part of the bush (the presence of the flat means that the focusing calculation is simpler). A perspex probe holder 35 screwed to the steel bush holder 32 keeps the ultrasound transducer 34 in place and contains the water coupling medium 36 between the transducer 34 and the brass bush 31. The lubricant film is indicated by reference numeral 37 in FIGS. 11A and 11B.

The rig is capable of being run at any speed between 180 rpm and 2300 rpm. Loading is achieved by hanging dead weights from wires accommodated in grooves 38 around the circumference of the steel bush-holder 32. This design is intended to avoid distortion of the holder 32 and bush 31. The weights used can be, for example, 10 kg and 20 kg.

Figure 12:
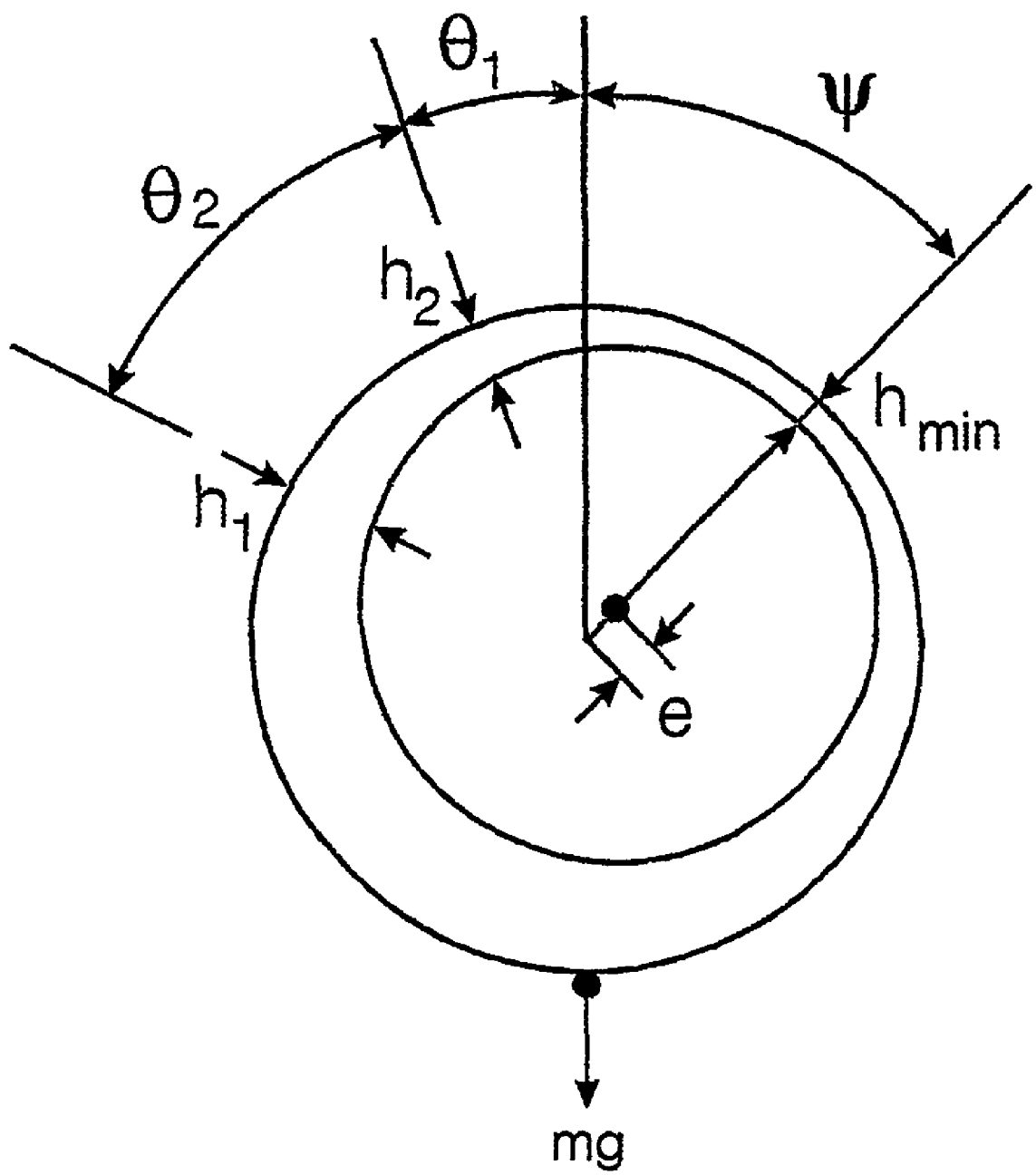
FIG. 12 shows the notation used in derivation of the attitude angle and minimum film thickness equations.

The angular position of the transducer 34 can be varied by rotating the bush 31 and holder 32 arrangement around the shaft 30. Referring to FIG. 12, the attitude angle $\psi$ is the angle that the line joining the centres of the shaft 30 and bush 31 makes with a vertical line. The eccentricity, e, is the distance between the shaft and bush centres. The film thickness $h_\theta$ at position $\theta$ is related to the angle $(\theta+\psi)$ by $h = c(1+\cos(\theta+\psi))$. If two values of $h_\theta$ are recorded at separate locations, then the attitude angle, $\psi$, and the minimum film thickness, $h_{min}$, can be deduced. For each experimental condition, two film thickness measurements $h_{\theta 1}$ and $h_{\theta 2}$ were obtained at two different angles $\theta_1$ and $\theta_2$ as shown in FIG. 12. From this information it is possible to work out the attitude angle and the eccentricity from $$\Rightarrow \psi = \arctan\left[\frac{(h_{\theta 2} - c) - \frac{\cos\theta_2}{\cos\theta_1}(h_{\theta 1} - c)}{\frac{\sin\theta_2}{\sin\theta_1}(h_{\theta 1} - c) - (h_{\theta 2} - c)}\tan\theta_1\right]$$

and $$e = \frac{c - h_{\theta 1}}{\cos(\theta_1 - \psi)} \text{ or } e = \frac{c - h_{\theta 2}}{\cos(\theta_1 - \psi)}$$

Temperature is monitored by use of thermocouples. The thermocouples are mounted in 2 mm diameter holes drilled into the steel bush-holder 32 and through to the brass bush 31. The holes terminate 1 mm short of the bearing surface of the brass bush 31.

Three types of oil were used in these tests, viz. Shell Turbo T68 and Shell Tellus T46 and Dow Corning Silicone Fluid 210H. The kinematic viscosities of these oil are shown in Table 1 below whilst their densities are shown in Table 2.

TABLE 1

Viscosities of the oils used

| Temperature | Turbo T68 | Tellus T46 | Silicone 210H |
|---|---|---|---|
| 40° C. | 68 cSt | 46 cSt | 75 cSt |
| 100° C. | 9.8 cSt | 8.1 cSt | 32 cSt |

The speed of sound in the oils varies from oil to oil and changes slightly with temperature. The speeds measured at 25° C. are shown for each oil in Table 3 below.

TABLE 2

Densities of the oils at 15° C.

| Oil | Turbo T68 | Tellus T46 | Silicone 210H |
|---|---|---|---|
| Density (g/cm) | 0.876 | 0.876 | 0.96 |

TABLE 3

Speed of propagation of ultrasound in the oils at 25° C.

| Oil | Turbo TGB | Tellus T46 | Silicone 210H |
|---|---|---|---|
| Velocity (ms$^{-1}$) | 1386 | 1181 | 831 |

The film thickness variation for hydrodynamic journal bearings is usually expressed as plots of the eccentricity ratio, $\epsilon$, against Sommerfeld number, S, where, $$\varepsilon = \frac{e}{c} = \frac{c - h_{min}}{c},$$

$$S = \eta\omega\frac{LD}{W}\left(\frac{R}{c}\right)^2$$

and L is the length of the bearing, D is its diameter and R the radius, W is the load, c is the radial clearance between the bearing and the shaft, $h_{min}$ the minimum film thickness and q is the dynamic viscosity.

Figure 13:
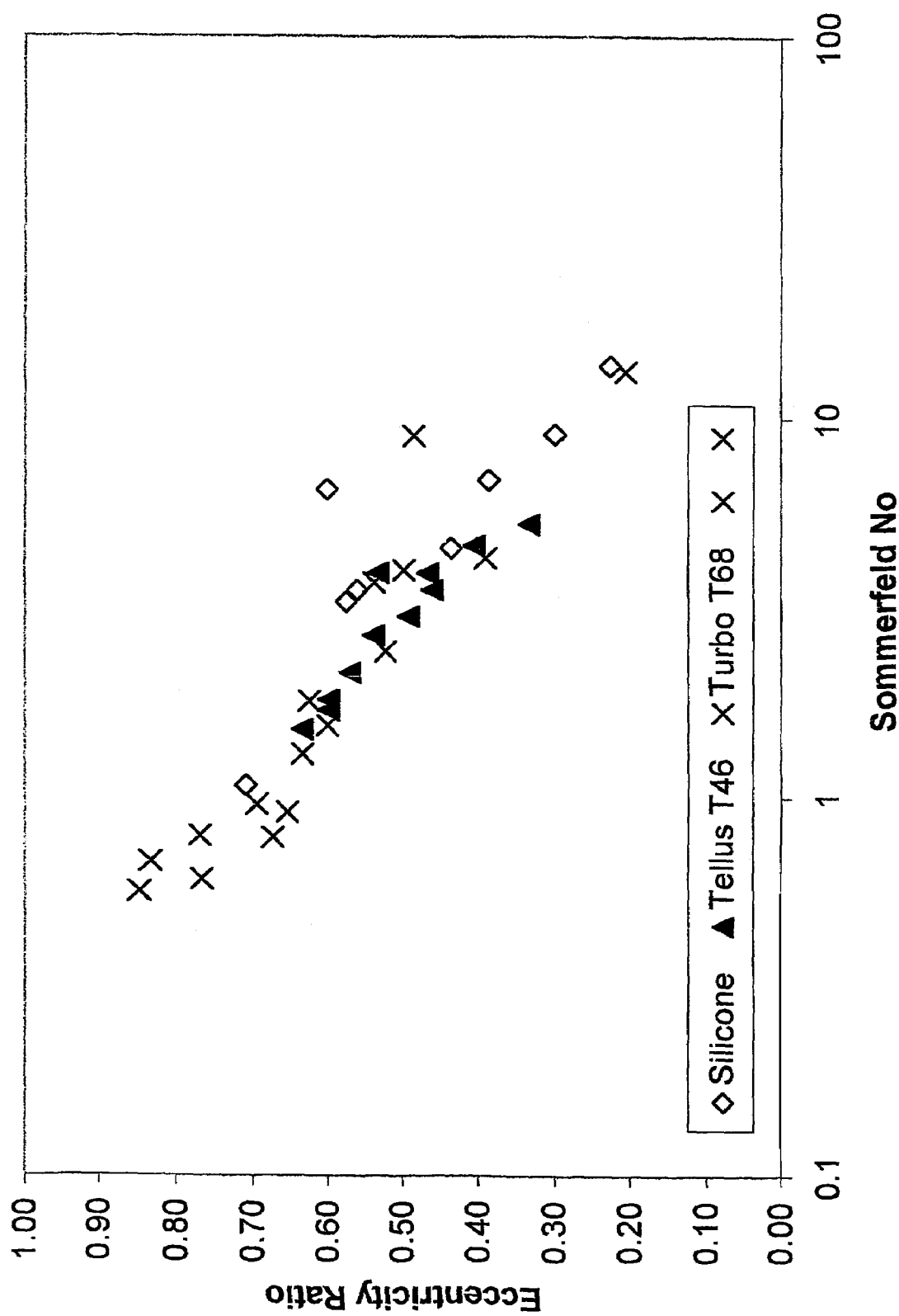
FIG. 13 shows dynamic test results for the journal bearing.

If the lubricant is Newtonian and isoviscous then film thickness and various bearing loads, speeds and fluid viscosities should all collapse onto a single line. FIG. 13 shows the results for three different oils. The results do collapse onto a single curve. It should be remembered that this is a dynamic process and some scatter is expected.

Rotating Ball Tests

Figure 14:
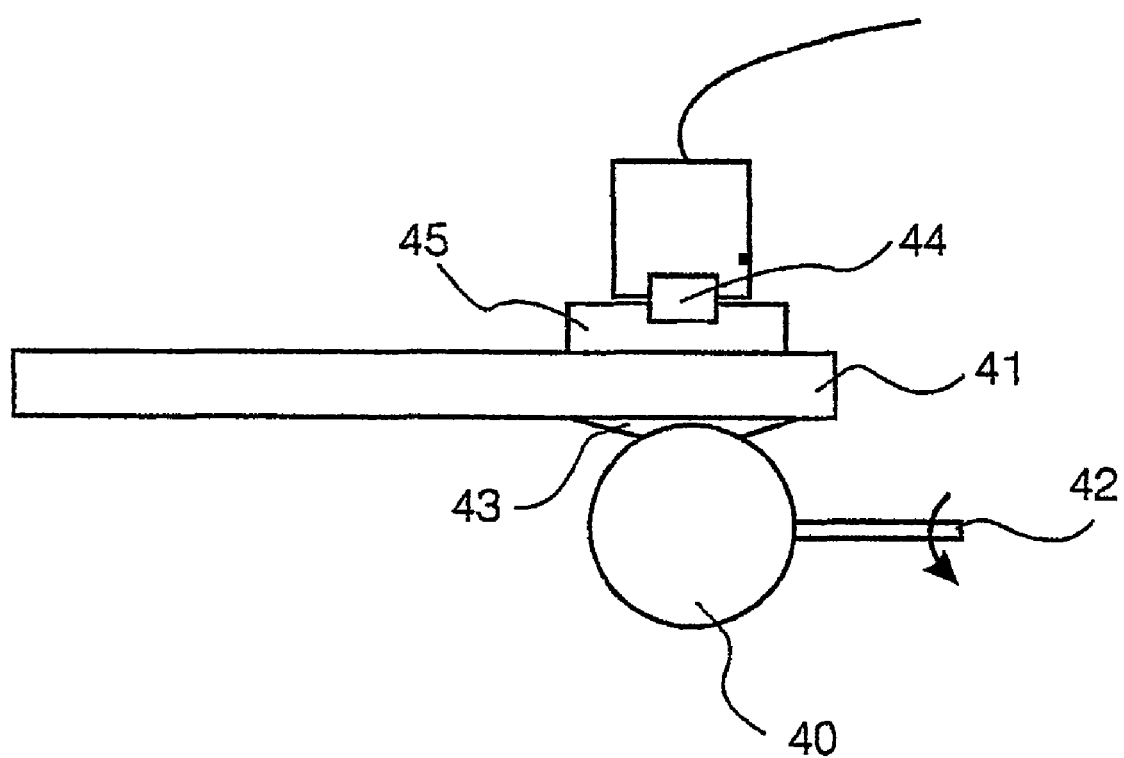
FIG. 14 is an outline of the principal components used in a ball on flat elastohydrodynamic lubricated contact rig.

The purpose of this test configuration is to prove the method on an elastohydrodynamic lubricant film (of the type found for example in rolling bearings, gears, cam/tappets). FIG. 14 shows a schematic of the apparatus whereby a steel ball 40 is loaded against the underside of a flat disk 41 which is submerged in oil (Shell Turbo T68). The ball is rotated by a drive shaft 42 at constant velocity and lubricant is entrained into the contact between the ball and the disk; an elastohydrodynamic film 43 forms between the surfaces. The ultrasonic transducer 44 (in this instance a 50 MHz focussing probe) is mounted above the disk such that the wave passes through a water coupling medium 45 and focuses on the contact patch (the contact between the ball and the disk).

Figure 15:
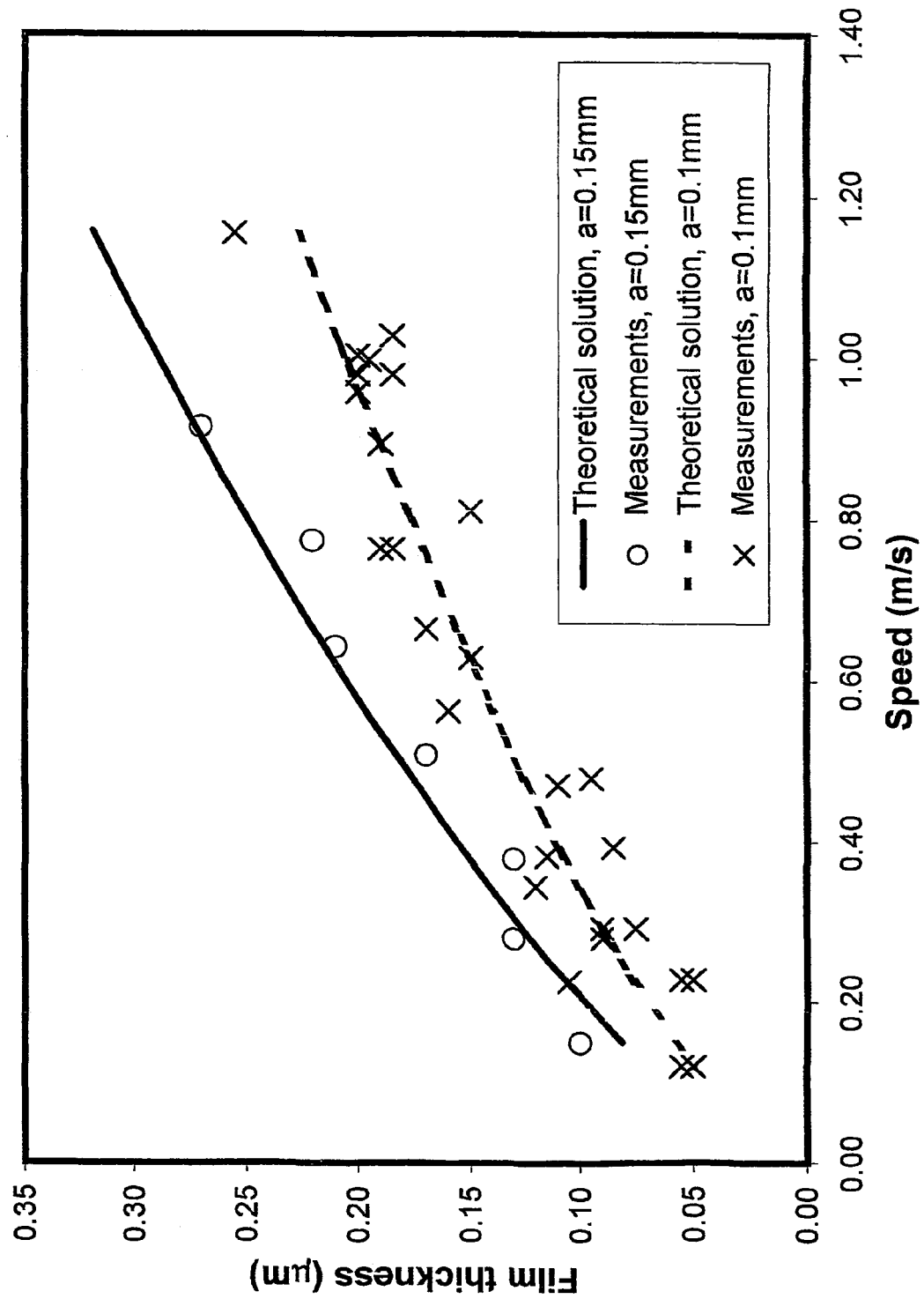
FIG. 15 shows the film thickness as a function ball sliding speed in the ball on flat elastohydrodynamic lubricated contact rig.

The reflected ultrasonic pulses are recorded and the Spectral gradient method is used to determine the lubricant film thickness. The data points on FIG. 15 shows the measured film thickness as it varies with the rotational speed of the ball for two different applied loads. The solid lines on FIG. 15 show the theoretical solution for the film thickness which has been determined by numerical calculation [Dowson, D. and Higginson, G. R. (1977), 'Elasto-Hydrodynamic Lubrication, 2nd ed.' Pergamon Press]. Good agreement is observed.

Figure 16:
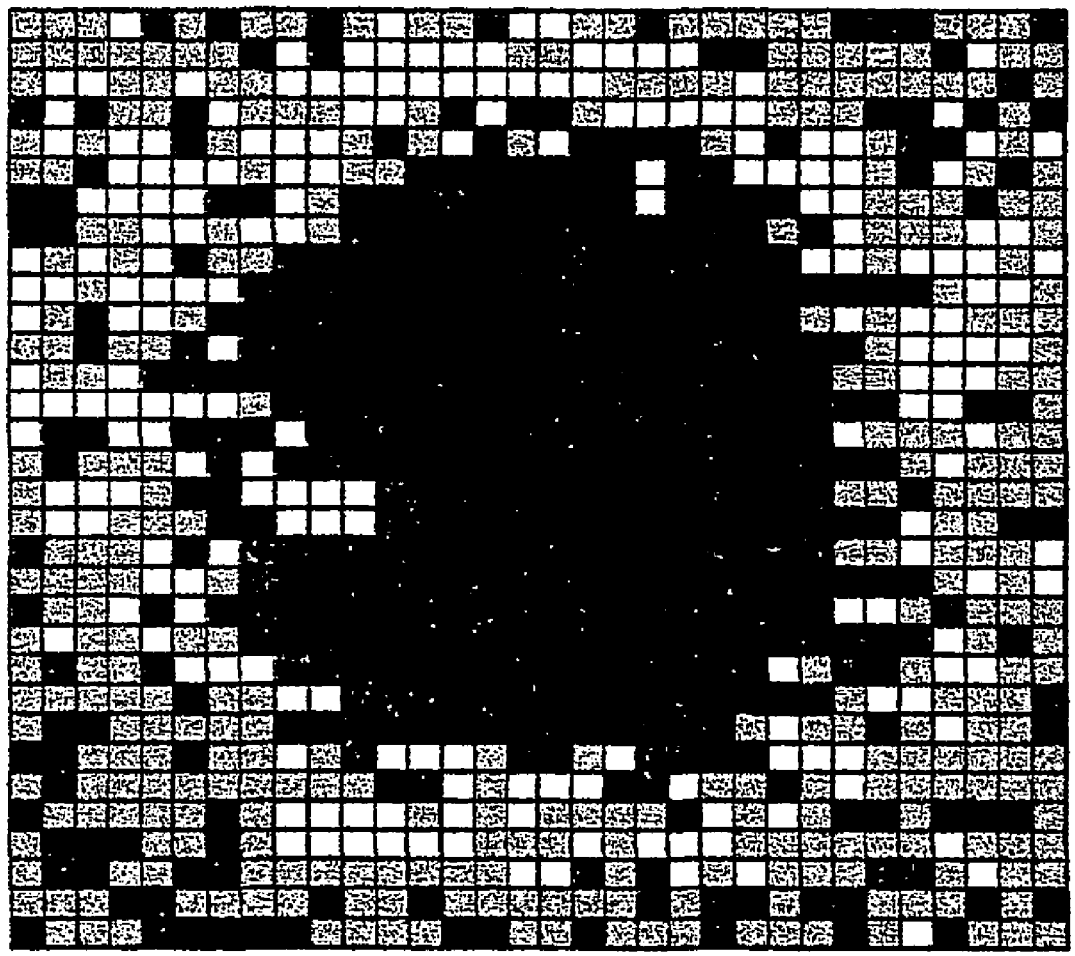
FIG. 16 shows a map of the film over the whole contact region in the ball on flat elastohydrodynamic lubricated contact rig.

Further, the ultrasonic probe is rastered in a horizontal plane such that the focussed wave scans across the contact. The film thickness is monitored throughout this movement to build up a map over the contact. FIG. 16 shows this map.

Rolling Element Bearing Tests

One of the most common industrial cases of elastohydrodynamic lubrication is the oil film that forms between the rolling elements-(balls or rollers) in a rolling element bearing. In this experimental procedure the teaching of the disclosure are used to measure the thickness of that film on-line during bearing operation.

Figure 17:
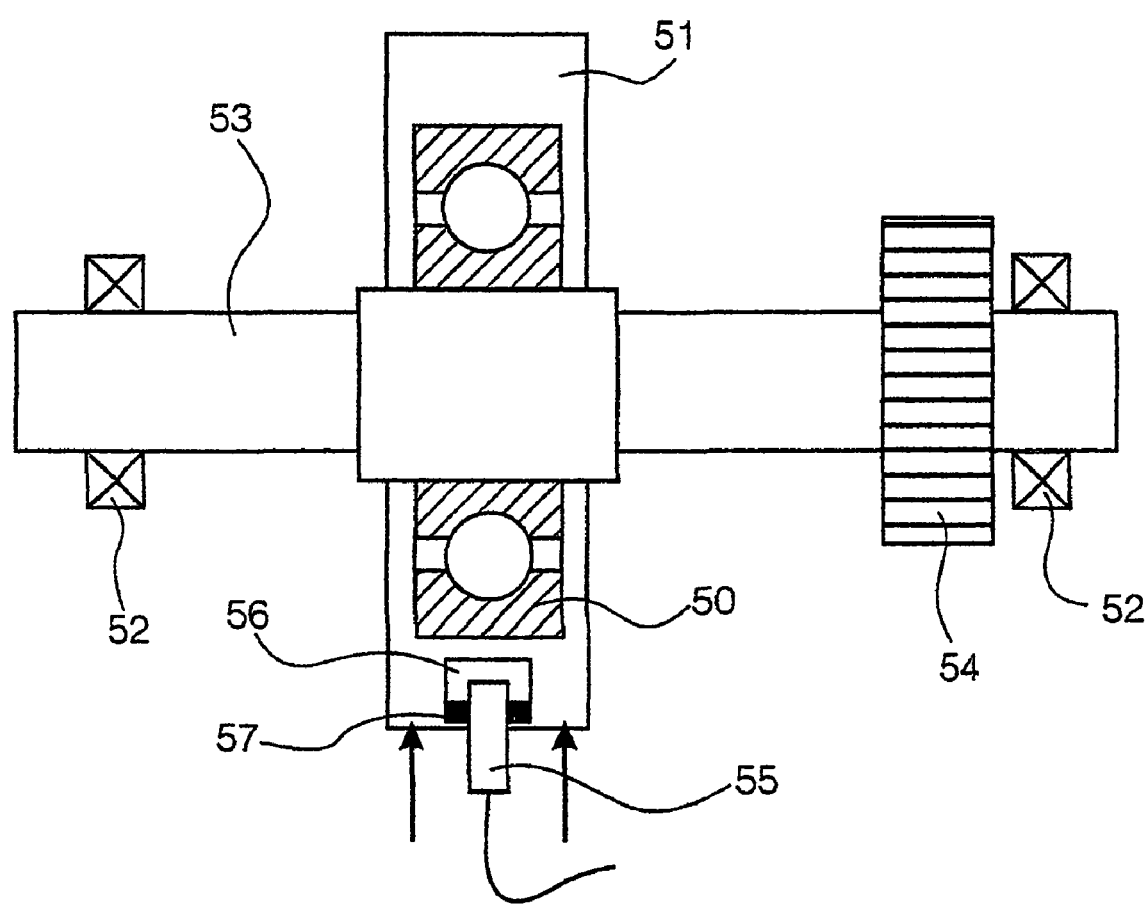
FIG. 17 is an outline of the principal components used in a lubricated rolling bearing test rig; and, FIG. 18 shows the film thickness as a function of the time of operation determined from the rolling bearing test rig.

FIG. 17 shows the apparatus; a deep groove ball bearing (part number SKF 6410) 50 is mounted inside a housing 51 which is loaded by means of a hydraulic actuator. A shaft 53 is located inside the inner raceway of the rolling bearing and is supported in two plumber blocks 52. The shaft is driven through a pulley 54 and electric motor (not shown). The transducer 55 (in this application a 25 MHz focussing probe) is mounted in a recess in the housing. The transducer is coupled to the housing recess floor by means of a water coupling medium 56 and held in place by an o-ring 57.

Figure 18:
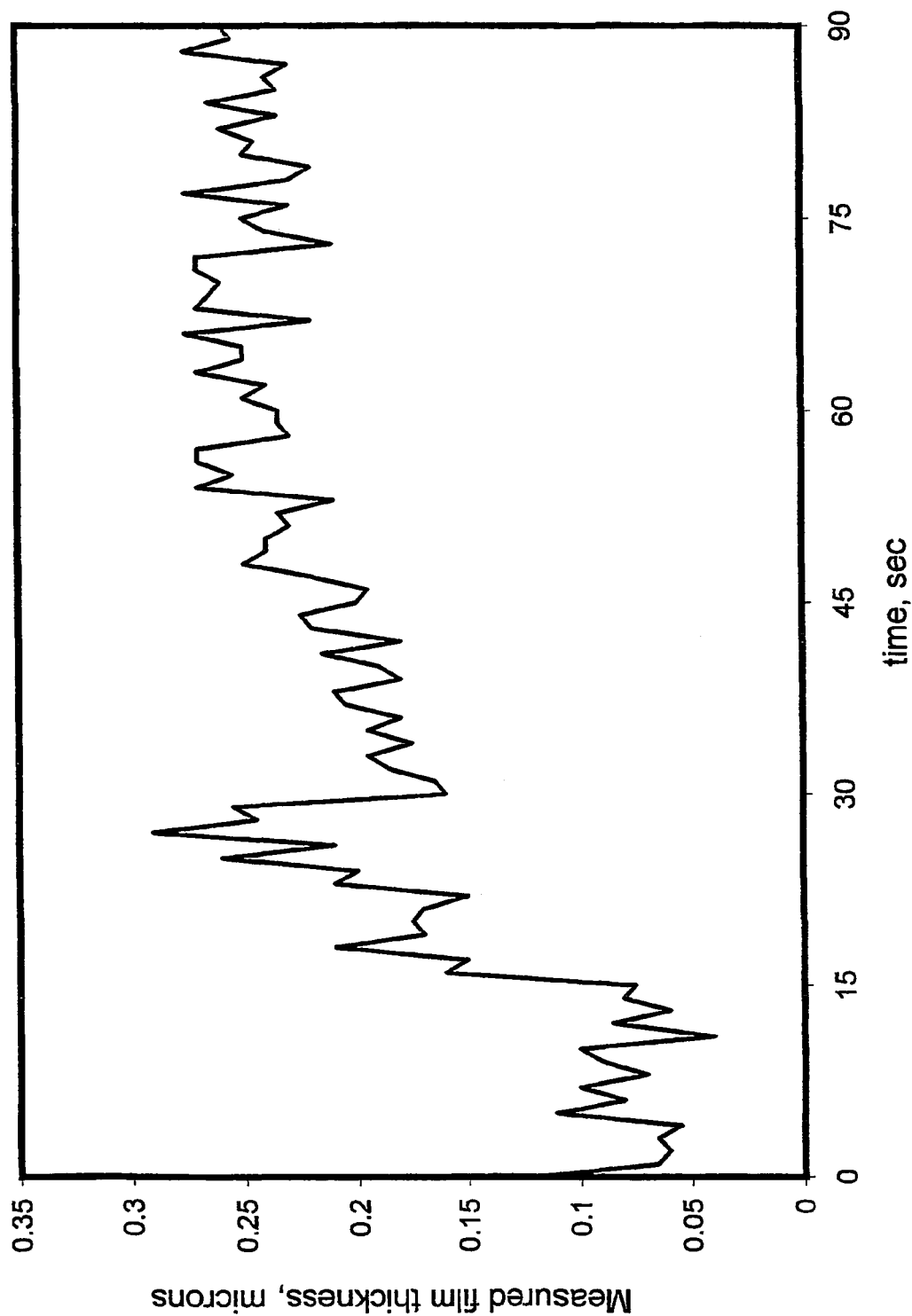

The reflected ultrasonic pulses are recorded and the Spectral gradient method is used to determine the lubricant film thickness. The algorithms for the calculation are carried out in real time and a continuous monitoring of the lubricant film thickness is displayed on the PC screen FIG. 18 shows a set of film thickness-measurements for the rolling bearing operating with Shell Turbo T68 lubricant.

Discussion

The work presented here has shown how the teachings of the disclosure can be used to measure a wide range of lubricant film thicknesses encountered in practical lubricated machinery. The approach requires the selection of an appropriate transducer and signal processing algorithm. By these methods and using conventional transducers the minimum film thickness measurable is approximately 10 nanometeres. There is no upper limit to the measurable thickness.

For film thicknesses below this level the roughness of the surface is an important factor. Films are therefore only coherent for very smooth surfaces. In this region the use of shear wave transducers is necessary. This is because the oil becomes much more viscous in the near surface region and under the extreme pressures [Williams J A. *Engineering Tribology*, page 326. Oxford University Press, 1998]) allowing ultrasound shear waves to propagate with a velocity which is much slower than that of longitudinal waves.

The present invention disclosure offers the following advantages over existing methods of film measurement:
   (i) The ultrasound beam propagates directly through the bearing material itself, eliminating the requirement for any form of window, or significant modification of the bearing.
   (ii) By selection of an appropriate transducer and processing algorithm it is capable of providing accurate measurements over a very wide range of film thickness.
   (ii) It is capable of providing a rapid response time (currently <0.1 s but potentially much faster), calculation in real time, and hence online measurements.
   (iii) It provides localised measurements (typical spot size of focused ultrasound beam is 100 μm).
   (iv) Electrical isolation of the two bearing elements is not necessary as with electrical methods such as the capacitance method.
   (v) Measuring probes are small and can fit into tightly packed bearing systems and machinery.

There are numerous potential areas of industrial application for the present disclosure. These range from research and development application to field use.

As a research tool, the present disclosure could be used in the design and optimisation of machine elements (such as rolling bearings, journal bearings, cam/tappets, piston rings, thrust pad bearings, fluid seals). It would also be particularly valuable to lubricant developers in relating film thickness to oil properties, eg shear rate dependence.

In field use, the teachings of the disclosure will have applications in online monitoring of components such as bearings, seals, gears and thrust pads found in the automotive, power production and process industries. Such online monitoring could be carried out by highly dedicated, cheaper, mass-production variants of the research equipment currently used. The disclosure may find application in fields other than those involving lubricants.

The invention claimed is:

1. A method of determining the thickness of a film disposed between two bodies in a two body interface assembly, the method comprising propagating an ultrasound wave towards the film; measuring a reflection coefficient from a reflection of said ultrasound wave at an interface including said film, said reflection coefficient being indicative of a proportion of the ultrasound wave which is reflected at said interface; and determining the thickness by quantifying the stiffness of the film from said reflection coefficient in conjunction with at least one of the group consisting of: a spring model of said assembly and continuum model of said assembly.

2. The method as claimed in claim 1 wherein the ultrasound wave is propagated through the first of said two bodies substantially normal to an interface between said film and said first body ("the first interface").

3. The method as claimed in claim 2 further comprising the step of detecting the proportion of the ultrasound wave which is reflected at said interface.

4. The method as claimed in claim 1 further comprising the step of detecting the proportion of the ultrasound wave which is reflected at the interface between the second of said two bodies and the film ("the second interface").

5. The method as claimed in claim 1 further comprising the step of detecting the proportion of the ultrasound wave which is transmitted through said two bodies and said film.

6. The method as claimed in claim 1 wherein a single transducer is used both to generate the ultrasound wave and detect the reflection thereof.

7. The method as claimed in claim 1 wherein the ultrasound wave is propagated through a coupling medium towards said first body.

8. The method as claimed in claim 7 wherein said coupling medium comprises water.

9. The method as claimed in claim 1 including the step of determining film thickness from the shape and gradients contained within a whole measurable reflection frequency spectrum.

10. The method as claimed in 1 further including the step of determining film thickness from a region where the reflection coefficient is linearly proportional to frequency.

11. The method as claimed in claim 1 wherein said two bodies are parts of a lubricated bearing such as a journal bearing, roller element bearing, piston-ring liner, cam-tappet, wet seal, thrust pad bearing or gear teeth.

12. The method as claimed in claim 1 further comprising measuring and performing a frequency spectrum analysis on said reflection of said ultrasound wave.

13. The method as claimed in claim 12 wherein the film thickness is determined from the shape and gradients of the frequency spectrum over a frequency range below the resonant frequency of the film.

14. The method as claimed in claim 1 wherein said film is a lubricant film.

15. The method as claimed in claim 1 wherein said film has a thickness less than 10 microns.

16. An apparatus for determining the thickness of a lubricant film comprising:
   means for generating an ultrasound wave and propagating same towards a film whose thickness it is desired to determine;
   a detector for detecting a reflection coefficient from a reflected part of said ultrasound wave which has been reflected at an interface including said film, said reflection coefficient being indicative of a proportion of the ultrasound wave which is reflected at said interface; and
   a processor for determining the thickness of the film by quantifying the stiffness of the film from said reflection coefficient in conjunction with at least one of the group consisting of: a spring model and continuum model.

* * * * *